US006207702B1

(12) United States Patent
Schmitz et al.

(10) Patent No.: US 6,207,702 B1
(45) Date of Patent: Mar. 27, 2001

(54) METHOD FOR REDUCING POSTPRANDIAL OXIDATIVE STRESS USING COCOA PROCYANIDINS

(75) Inventors: Harold H. Schmitz, Branchburg; Leo J. Romanczyk, Jr., Hackettstown, both of NJ (US)

(73) Assignee: Mars, Incorporated, McClean, VA (US)

( * ) Notice: Subject to any disclaimer, the term of this patent is extended or adjusted under 35 U.S.C. 154(b) by 0 days.

(21) Appl. No.: 09/441,644

(22) Filed: Nov. 17, 1999

(51) Int. Cl.$^7$ .................................................. A61K 31/35
(52) U.S. Cl. ...................... 514/453; 514/456; 424/195.1; 426/72; 426/479; 426/593; 426/631; 426/655; 426/804
(58) Field of Search .......................... 424/195.1; 514/453, 514/456; 426/72, 593, 479, 631, 655, 804

(56) References Cited

U.S. PATENT DOCUMENTS 6,015,913 * 1/2000 Kealey et al. ........................ 549/386

* cited by examiner

*Primary Examiner*—Frederick Krass
(74) *Attorney, Agent, or Firm*—Margaret B. Kelley; Clifford Chance Rogers & Wells, LLP

(57) ABSTRACT

A method for reducing postprandial oxidative stress and associated pathologies by the dietary intake of cocoa procyanidins, such as epicatechin is disclosed.

32 Claims, 2 Drawing Sheets

METHOD FOR REDUCING POSTPRANDIAL OXIDATIVE STRESS USING COCOA PROCYANIDINS

FIELD OF THE INVENTION

This invention relates to a method for reducing postprandial oxidative stress.

BACKGROUND OF THE INVENTION

Studies have linked certain dietary factors with atherosclerosis, a forerunner of coronary heart disease (Addis, P. B., Carr, T. P., Hassel, C. A., Hwang, Z. Z., Warner, G. J., Atherogenic and anti-atherogenic factors in the human diet. *Biochem. Soc. Symp.* 61, 259–271 (1995)). For example, a diet high in polyunsaturated fatty acids (PUFAS) may render low-density lipoprotein (LDL) more susceptible to peroxidation (Addis et al. 1995). The peroxidation of LDL can cause tissue damage leading to atherosclerosis (Sarkkinen, E. S., Uusitupa, M. I. J., Nyyssönen, K., Parviainen, M., Penttila, I., Salonen, J. T., Effects of two low-fat diets, high and low in polyunsaturated fatty acids, on plasma lipid peroxides and serum vitamin E levels in free-living hypercholesterolaemic men. *European Journal of Clinical Nutrition* (1993) 47: 623–630). The peroxidation of LDL is a result of the neutrophilic production of a superoxide anion radical or other reactive species (Steinberg, D., Parthasapathy, S., Carew, T. E., Khoo, J. C., Witztum, J. L. (1989) Beyond cholesterol. Modifications of low-density lipoprotein that increases its atherogenicity. *New England Journal of Medicine* 320: 915–924). The reactive species produced interact with PUFAS to form lipid peroxyl radicals, which subsequently produce lipid hydroperoxides and additional lipid peroxyl radicals (Steinberg et al. 1989). This initiates a peroxidative cascade which may eventually modify an essential part of the lipid's membrane, causing changes in membrane permeability and even cell death (Steinberg et al. 1989). Peroxidative degradation of LDL also leads to the formation of lipid oxidation products such as malondialdehyde (MDA) and other aldehydes which may be potentially toxic to the cell (Steinberg et al. 1989).

Oxidative stress has been implicated in a variety of diseases and pathological conditions, including endothelial cell cytotoxicity, coronary heart diseases (such as thrombosis and hyperlipemia) and cancer. (Addis et al. 1995). Recent studies have shown that elevated lipid peroxidation levels (oxidative stress) may play a role in the pathogenesis of Alzheimer's disease which includes a group of neurodegenerative disorders with diverse etiologies, but the same hallmark brain lesions. Practico D. et al., *Increased F2-isoprostanes in Alzheimer's disease: evidence for enhanced lipid peroxidation in vivo.* FASEB J. 1998 Dec.; 12 (15): 1777–1783.

Clinical studies have established that elevated plasma concentrations of LDL are associated with atherosclerosis, a most prevalent cardiovascular disease and the principle cause of heart attack, stroke and vascular circulation problems (Sarkkinen et al. 1993). It is believed that a reduction of atherogenic lipid peroxides (which are transported in the LDL fraction of blood serum) can reduce the risk of atherogenesis (Mazur, A., Bayle, D., Lab, C., Rock, E., Rayssiguier, Y., Inhibiting effect of procyanidin-rich extracts on LDL oxidation in vitro. *Atherosclerosis* 145 (1999) 421–422). Antioxidants limit oxidative modification of LDL and consequently lower plasma concentrations of LDL, thereby acting as anti-atherogenic compounds (Sarkkinen et al. 1993). The oxidation of LDL has been reported as a model for testing the ability of polyphenols to act as antioxidants by breaking the peroxidative cascade described above (Rice-Evans, C., Plant polyphenols: free radical scavengers or chain-breaking antioxidants? Biochem. Soc. Symp. 61, 103–116 (1995)). Studies have reported that polyphenols can break the chain of the peroxidative process by intercepting free radicals before they reenter the cycle (Rice-Evans 1995).

SUMMARY OF THE INVENTION

This invention is directed to a method for reducing postprandial oxidative stress and associated pathologies by the dietary intake of cocoa polyphenols, including cocoa procyanidins. Cocoa procyanidins include monomers and dimers of catechin and epicatechin.

Cocoa procyanidins can be obtained from several *Theobroma cacao* genotypes by the procedures discussed hereinafter. Cocoa procyanidins can also be obtained by synthetic methods described in PCT/US98/21392 (published as WO 99/19319 on Apr. 22, 1999) which is incorporated herein by reference. The oligomers synthesized using these methods may be linear, having the structure:

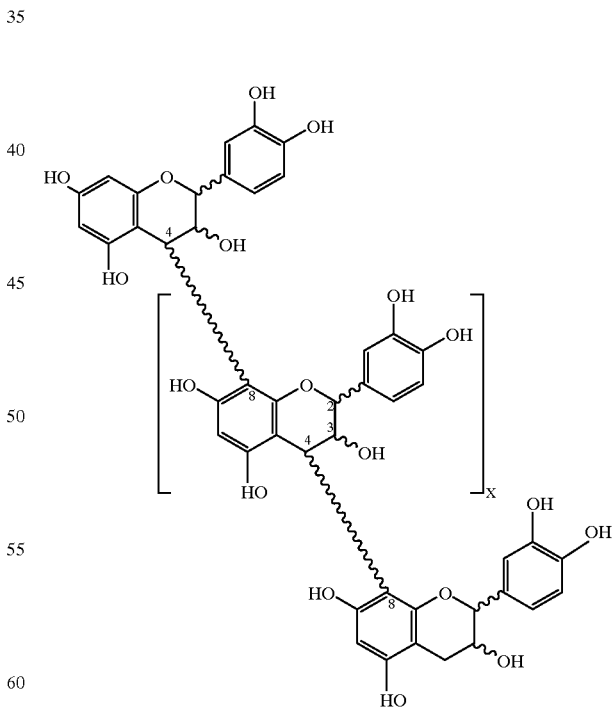

where X is an integer from zero to sixteen or branched, having the structure:

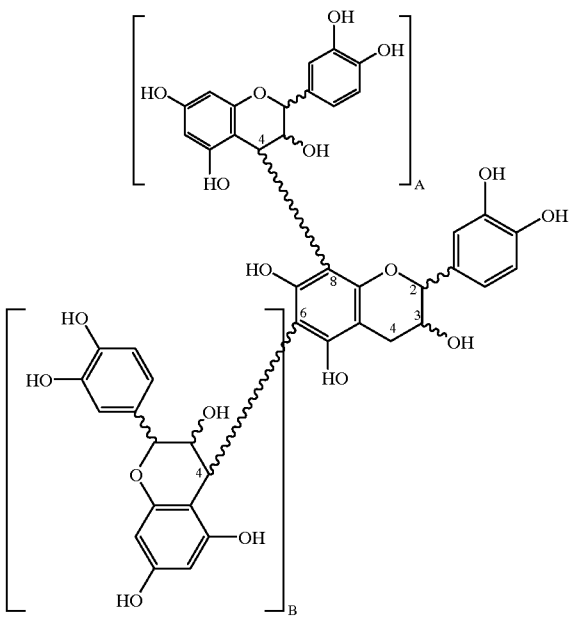

where A and B are independently integers from one to fifteen.

It has been found that the dietary intake of an effective amount of cocoa procyanidins counteracts postprandial oxidative stress which has been linked to associated pathologies as described herein. Postprandial oxidative stress occurs following the ingestion of food products and has been linked with hyperlipidemia and increased risk of cardiovascular disease. Ursini F. et al., *Postprandial plasma lipid hydroperoxides: a possible link between diet and atherosclerosis.* Free Radic. Biol. Med. 1998 Jul. 15; 25 (2): 250–252. Consequently, the dietary intake of an effective amount of cocoa procyanidins counteracts these pathologies associated with postprandial oxidative stress.

Measuring the formation of lipid oxidative products is one way to assay oxidative stress. Cocoa procyanidins reduce LDL peroxidation which consequently reduces the formation of lipid oxidation products which can be assayed as described herein. One such lipid oxidation product is malondialdehyde (MDA) which may be potentially toxic to the cell. Cocoa procyanidins can be found in foods common in the human diet, including chocolate. Epicatechin is a cocoa procyanidin abundant in chocolate.

DETAILED DESCRIPTION OF THE INVENTION

Figure 1:
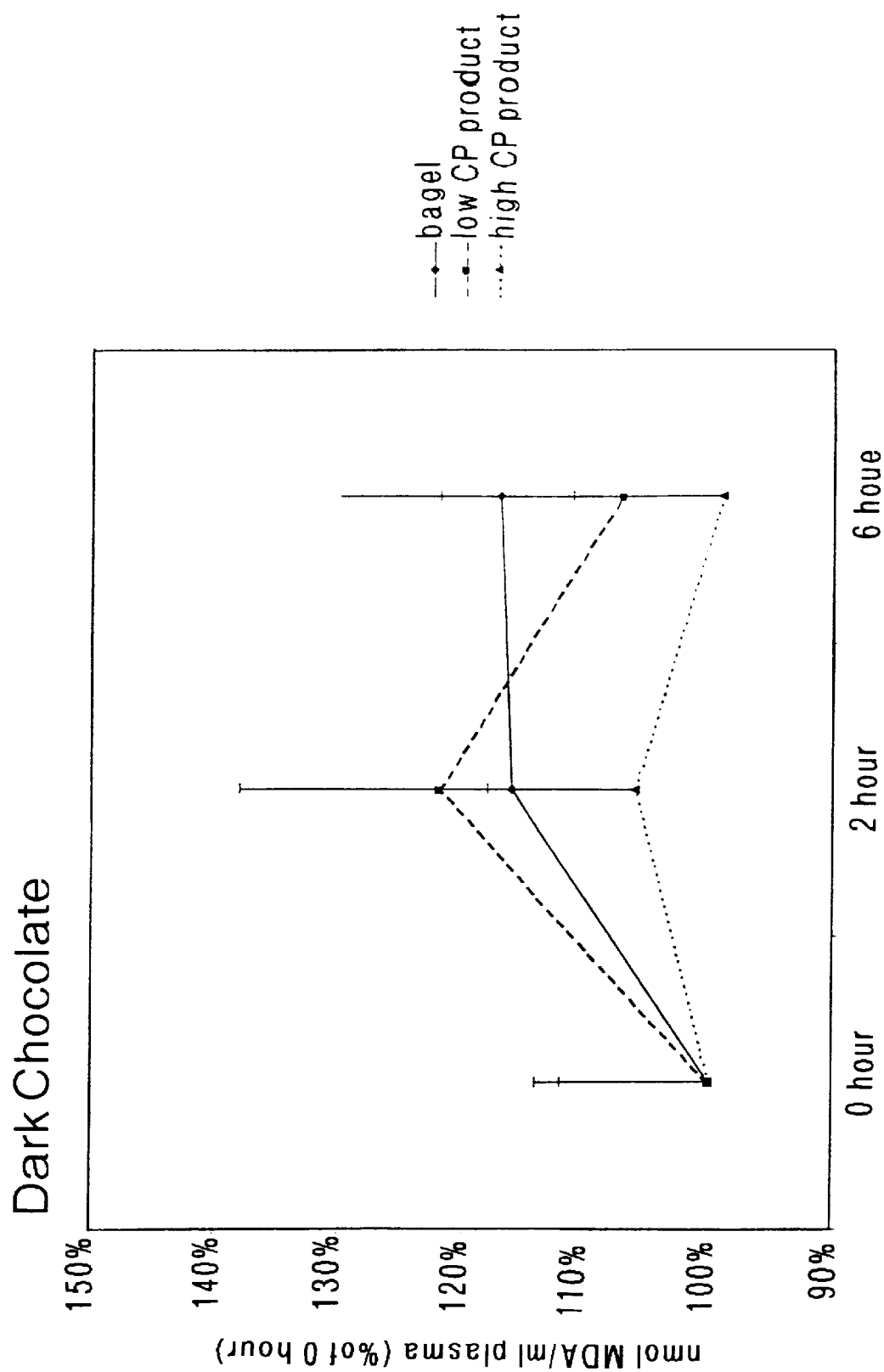
FIG. 1 shows the nanomoles (nmol) of malondialdehyde (MDA) in plasma at 2 and at 6 hours following ingestion of ½ bagel and a dark chocolate product which was made with enhanced levels of cocoa polyphenols and following ingestion of ½ bagel and a control chocolate containing lower levels cocoa polyphenols, including cocoa procyanidins (CPs).

It has been found that the dietary intake of cocoa procyanidins counteracts oxidative stress as measured by reduction of LDL peroxidation. Consequently, there was reduction in the formation of LDL peroxidation products, such as malondialdehyde (MDA), which may be potentially toxic to the cell. Plasma lipid peroxides were measured photometrically using a thiobarbituric acid (TBA) reaction based on methods described in Yagi, K., *Assay for blood plasma or serum,* Methods in Enzymology 105: 328–331 (1984) Academic Press, Inc., Orlando, Fla. (Ed. L. Packer). MDA is a low molecular weight end-product that forms via decomposition of the products formed by lipid peroxidation. The MDA found in the plasma can be quantified using the Yagi et al. methods because at low pH and elevated temperature, MDA reacts with TBA to generate a fluorescent red adduct of MDA and TBA (1:2 ratio). The fluorescent intensity of the MDA:TBA adduct, which can be accurately quantified, parallels the concentration of the adduct. Hence, the amount of lipid peroxide produced can be fluorometrically measured using the TBA reaction, using an MDA standard. Substances other than the lipid peroxides can react with TBA and thereby distort results. These water-soluble substances are eliminated from the plasma sample by isolating the lipids using precipitation along with the serum protein using a phosphotungstic acid-sulfuric acid system.

As shown below, levels of MDA decreased at 2 and at 6 hours following ingestion of semisweet chocolate high in cocoa polyphenols. Similarly, MDA levels decreased at 2 and at 6 hours following ingestion of dark chocolate high in cocoa polyphenols. The decreases were more pronounced when the intake of chocolate was increased. MDA levels also decreased (albeit not as much) when tested at 6 hours following ingestion of a dark chocolate which contained less of the cocoa polyphenols (that is, lower amounts of cocoa polyphenols than contained in the test chocolates). All of the chocolates used in the experiments described herein were made using the methods discussed hereinafter. All test products contained enriched levels of cocoa procyanidins.

For example, the dark chocolate test product contained 147 mg total cocoa procyanidins (40.6 mg monomer) per 36.9 gram test product. The dark chocolate control product contained only 3.3. mg cocoa procyanidins (1.8 mg monomers) per 36.9 gram control product. The semisweet products contained 185 mg total cocoa procyanidins (45.3 mg monomers) per a 35 gram bag of semisweet chocolate bits. A single bag serving was consumed as the single dosage size. A two bag serving (70 grams) of semisweet chocolate bits product contained 370 mg total cocoa procyanidins and a three bag serving (105 grams) of semisweet chocolate bits product contained 555 mg total cocoa procyanidins.

The quantities of cocoa procyanidin monomers and oligomers in the test products were measured by the analytical methods discussed hereinafter. Procyanidin levels were determined by analyzing levels of chocolate liquor or jet black cocoa powder and calculating the percentage of powder in the final product. The low levels of procyanidins in the control dark chocolate product precluded direct analysis.

The chocolate liquor used to make the test products and the control product was a blend of cocoa beans, some of which were underfermented. The beans were prepared by the methods described in PCT/US97/15893 (published as WO 98/09533 on Mar. 12, 1998), which is herein incorporated by reference. Standard of Identity rules governed the different levels of chocolate liquor and sugar which were used to prepare semisweet versus dark chocolate. The semisweet chocolate had higher levels of chocolate liquor and sugar. The semisweet chocolate and the dark chocolate test products were used to demonstrate that even though the cocoa procyanidins were delivered using two different forms of test products, similar effects were exhibited by each.

Methods for preparing cocoa mass are described in U.S. Pat. No. 5,554,645 (issued Sep. 10, 1996) which is herein incorporated by reference. Harvested cocoa pods were opened and the beans with pulp were removed for freeze-drying. The pulp was manually removed from the freeze-dried mass and the beans were subjected to the following manipulations. The freeze-dried cocoa beans were first manually dehulled and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

The chocolate liquor and/or cocoa solids can be prepared by roasting the cocoa beans to an internal bean temperature of 95° C. to 160° C., winnowing the cocoa nibs from the roasted cocoa beans, milling the roasted cocoa nibs into the chocolate liquor and optionally recovering cocoa butter and partially defatted cocoa solids from the chocolate liquor. The cocoa solids can be further defatted using conventional methods.

Alternatively, partially defatted cocoa beans having a high cocoa polyphenol content, i.e., a high cocoa procyanidin content, can be obtained by processing without a bean or nib roasting step and without milling the beans to chocolate liquor. Even higher levels can be achieved if underfermented cocoa beans are used in this process. This method conserves the cocoa polyphenols because it omits the traditional roasting step. The method consists essentially of the steps of: (a) heating the cocoa beans to an internal bean temperature just sufficient to reduce the moisture content to about 3% by weight and loosen the cocoa shell, typically using a infra red heating apparatus for about 3 to 4 minutes; (b) winnowing the cocoa nibs from the cocoa shells; (c) screw pressing the cocoa nibs; and (d) recovering the cocoa butter and partially defatted cocoa solids which contain cocoa polyphenols including cocoa procyanidins. Optionally, the cocoa beans are cleaned prior to the heating step, e.g., in an air fluidized bed density separator. Preferably, the cocoa beans are heated to an internal bean temperature of about 100° C. to about 110° C., more preferably less than about 105° C. The winnowing can be carried out in an air fluidized bed density separator. The above process of heating the cocoa beans to reduce the moisture content and loosen the cocoa shell is disclosed in U.S. Pat. No. 6,015,913 issued Jan. 18, 2000 (to K. S. Kealey, et al.). which is herein incorporated by reference.

The internal bean temperature (IBT) can be measured by filling an insulated container such as a thermos bottle with beans (approximately 80–100 beans). In order to maintain the temperature of the beans during transfer from the heating apparatus to the thermos, the insulated container is then appropriately sealed in order to maintain the temperature of the sample therein. A thermometer is inserted into the bean filled insulated container and the temperature of the thermometer is equilibrated with respect to the beans in the thermos. The temperature reading is the IBT temperature of the beans. IBT can also be considered the equilibrium mass temperature of the beans.

The cocoa beans can be divided into four categories based on their color: predominately brown (fully fermented), purple/brown, purple, and slaty (unfermented). Preferably, the cocoa solids are prepared from underfermented cocoa beans, i.e., slaty cocoa beans, purple cocoa beans, mixtures of slaty and purple cocoa beans, mixtures of purple and brown cocoa beans, or mixtures of slaty, purple, and brown cocoa beans. More preferably, the cocoa beans are slaty and/or purple cocoa beans have a higher cocoa polyphenol content than fermented beans.

The cocoa polyphenol content of cocoa ingredients, for example, the roasted cocoa nibs, chocolate liquor and partially defatted or nonfat cocoa solids, is higher when the cocoa beans or blends thereof have a fermentation factor of 275 or less. Preferably, these cocoa beans are used for processing into cocoa ingredients. The "fermentation factor" is determined using a grading system for characterizing the fermentation of the cocoa beans. For example, slaty beans are designated 1, purple beans as 2, purple/brown beans as 3, and brown beans as 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 [(50×1)+(50×20)].

Conventional processing techniques do not provide food products, especially confectioneries which adequately retain the cocoa polyphenol concentrations. However, high cocoa polyphenol food products may be prepared using conventional chocolate liquors or these high cocoa polyphenol chocolate liquors and/or conventional chocolate cocoa solids or high cocoa polyphenol cocoa solids by protecting the milk and/or sweetener with a pretreatment ingredient selected from the group consisting of an antioxidant, an emulsifier, a fat, a flavorant and mixtures thereof, before adding the cocoa ingredient. Preferred pretreatment ingredient is a mixture of cocoa butter and lecithin.

Examples of high cocoa polyphenol food products include pet food, dry cocoa mixes, puddings, syrups, cookies, savory sauces, rice mixes and/or rice cakes, beverages, including cocoa beverages and carbonated beverages. Preferably, the high cocoa polyphenol foods are chocolate confectioneries, for example, dark chocolate, semisweet chocolate, sweet chocolate, milk chocolate, buttermilk chocolate, skim milk chocolate, mixed dairy milk chocolate and reduced fat chocolate. Cocoa polyphenols may be added to white chocolate and white chocolate coating to create products with high levels of cocoa polyphenols. These confectioneries may be either Standard of Identity chocolates or non-Standard of Identity chocolates. Preferable non-chocolate food products include nut-based products such as peanut butter, peanut brittle and the like. Also included are low-fat food products prepared with defatted or partially defatted nut meats. Cocoa procyanidins are also used in dietary supplements and pharmaceuticals. Also included are food products comprising at least one cocoa polyphenol and L-arginine. The procyanidin and L-arginine may be provided, respectively, by cocoa and/or nut procyanidins and an L-arginine containing component, such as a nut meat. The L-arginine may be derived from any available arginine source, e.g., *Arachis hypogaea* (peanuts), *Juglans regia* (walnuts), *Prunus amygdalus* (almonds), *Corylus avellana* (hazelnuts), *Glycine max* (soy bean) and the like. The nut may be nut pieces, a nut skin, a nut paste, and/or a nut flour present in amounts which provide the desired amount of L-arginine, which will vary depending upon the nut source. The L-arginine-containing ingredient may also be a seed, a seed paste, and/or a seed flour. The cocoa polyphenols, including cocoa procyanidins, may be synthetic or natural. The procyanidins may from a source other than cocoa beans.

The food product may contain polyphenols, such as procyanidins, from a source other than cocoa, e.g., the polyphenols found in the skins of nuts such as those described above. Peanut skins contain about 17% procyanidins, and almond skins contain up to 30% procyanidins. In a preferred embodiment, the nut skins are used in the food product, e.g., the nougat of a chocolate candy. Polyphenols from fruits and vegetables may also be suitable for use herein. It is known that the skins of fruits such as apples and oranges, as well as grape seeds, are high in polyphenols.

As used herein "food" is a material consisting of protein, carbohydrate and/or fat, which is used in the body of an organism to sustain growth, repair vital processes, and to furnish energy. Foods may also contain supplementary substances, such as, minerals, vitamins, and condiments (Merriam-Webster Collegiate Dictionary, 10th Edition, 1993).

As used herein "food supplement" is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients. (Merriam-Webster Collegiate Dictionary, 10th Edition, 1993). When the term is used on food labels, "supplement" means that nutrients have been added in amounts greater than 50% above the U.S. Recommended Daily Allowance ("Understanding Normal and Clinical Nutrition, 3rd Edition, Editors Whitney, Cataldo and Rolfes at page 525).

As used herein "pharmaceutical" is a medicinal drug. (Merriam-Webster Collegiate Dictionary, 10th Edition, 1993).

The cocoa procyanidins in these products are part of a larger family of cocoa polyphenols which are present in cocoa beans. Suitable cocoa procyanidin-containing ingredients include roasted cocoa nibs or fractions thereof, chocolate liquor, partially defatted cocoa solids, nonfat cocoa solids, cocoa powder milled from the cocoa solids, and mixtures thereof. Preferably, the ingredients are prepared from underfermented beans since these beans contain higher amounts of cocoa polyphenols including the cocoa procyanidins. Cocoa procyanidins can be obtained from several *Theobroma cacao* genotypes which represent the three recognized horticultural races of cocoa, namely, Trinitario, Forastero and Criollo. See Engels, J. M. M., *Genetic Resources of Cacao: A catalogue of the CATIE collection, Tech. Bull.* 7, Turrialba, Costa Rica (1981). An extract containing cocoa polyphenols, including cocoa procyanidins, can be prepared by solvent extracting the partially defatted cocoa solids prepared from the underfermented cocoa beans or cocoa nibs having a fermentation factor of 275 or less, as described herein.

METHODS

Analytical Methods for the Quantification of Cocoa Procyanidins

The analytical method described below was used to separate and quantify, by degree of polymerization, the procyanidin composition of the seeds from *Theobroma cacao* and of chocolate. The analytical method described below is based upon work reported in Hammerstone, J. F., Lazarus, S. A., Mitchell, A. E., Rucker R., Schmitz H. H., *Identification of Procyanidins in Cocoa (Theobroma cacao) and Chocolate Using High-Performance Liquid Chromatography/Mass Spectrometry, J. Ag. Food Chem.;* 1999; 47 (10) 490–496. The utility of the analytical method described below was applied in a qualitative study of a broad range of food and beverage samples reported to contain various types of proanthocyanidins, as reported in Lazarus, S. A., Adamson, G. E., Hammerstone, J. F., Schmitz, H. H., *High-performance Liquid Chromatography/Mass Spectrometry Analysis of Proanthocyanidins in Foods and Beverages, J. Ag. Food Chem.;* 1999; 47 (9); 3693–3701. The analysis in Lazarus et al. (1999) reported analysis using fluorescence detection because of higher selectivity and sensitivity.

Composite standard stock solutions and calibration curves were generated for each procyanidin oligomer through decamer using the analytical method described below, as reported in Adamson, G. E., Lazarus, S. A., Mitchell, A. E., Prior R. L., Cao, G., Jacobs, P. H., Kremers B. G., Hammerstone, J. F., Rucker R., Ritter K. A., Schmitz H. H., *HPLC Method for the Quantification of Procyanidins in Cocoa and Chocolate Samples and Correlation to Total Antioxidant Capacity, J. Ag. Food Chem.;* 1999; 47 (10) 4184–4188. Samples were then compared with the composite standard to accurately determine the levels of procyanidins.

Extraction

The fresh seeds (from Brazilian cocoa beans) were ground in a high-speed laboratory mill with liquid nitrogen until the particle size was reduced to approximately 90 microns. Lipids were removed from 220 grams (g) of the ground seeds by extracting three times with 1000 milliliters (mL) of hexane. The lipid free solids were air dried to yield approximately 100 g of fat-free material. A fraction containing procyanidins was obtained by extracting with 1000 mL of 70% by volume acetone in water. The suspension was centrifuged for 10 minutes at 1500 g. The acetone layer was decanted through a funnel with glass wool. The aqueous acetone was then re-extracted with hexane (~75 mL) to remove residual lipids. The hexane layer was discarded and the aqueous acetone was rotary evaporated under partial vacuum at 40° C. to a final volume of 200 mL. The aqueous extract was freeze dried to yield approximately 19 g of acetone extract material.

Gel Chromatograhy

Approximately 2 g of acetone extract (obtained above) was suspended in 10 mL of 70% aqueous methanol and centrifuged at 1500 g. The supernatant was semi-purified on a Sephadex LH-20 column (70×3 centimeters) which had previously been equilibrated with methanol at a flow rate of 3.5 mL/min. Two and a half hours after sample loading, fractions were collected every 20 minutes and analyzed by HPLC for theobromine and caffeine See Clapperton, J., Hammerstone, J. F., Romanczyk, L. J., Yow, S., Lim, D., Lockwood, R., *Polyphenols and Cocoa Flavour, Proceedings,* 16th *International Conference of Groupe Polyphenols,* Lisbon, Portugal, Groupe Polyphenols: Norbonne, France, 1992; Tome II, pp. 112–115. Once the theobromine and caffeine were eluted off the column (~3.5 hours), the remaining eluate was collected for an additional 4.5 hours and rotary evaporated under partial vacuum at 40° C. to remove the organic solvent. Then the extract was suspended in water and freeze dried.

Purification of Procyanidin Oligomers by Preparative Normal-Phase HPLC

The cocoa extract from above (0.7 g) was dissolved in (7 mL) mixture of acetone/water/acetic acid in a ratio by volume of 70:29.5:0.5, respectively. A linear gradient (shown in the table below) was used to separate procyanidin fractions using a 5 μm Supelcosil LC column (Silica, 100 Angstroms (Å); 50×2 cm) (Supelco, Inc., Bellefonte, Pa.)

which was monitored by UV at a wavelength of 280 nanometers (nm).

| time (minutes) | methylene chloride/ acetic acid/ water (96:2:2 v/v)(%) | methanol/ acetic acid/ water (96:2:2 v/v)(%) | flow rate (mL/min) |
|---|---|---|---|
| 0 | 92.5 | 7.5 | 10 |
| 10 | 92.5 | 7.5 | 40 |
| 30 | 91.5 | 8.5 | 40 |
| 145 | 78.0 | 22.0 | 40 |
| 150 | 14.0 | 86.0 | 40 |
| 155 | 14.0 | 86.0 | 50 |
| 180 | 0 | 100 | 50 |

Fractions were collected at the valleys between the peaks corresponding to oligomers. Fractions with equal retention times from several preparative separations were combined, rotary evaporated under partial vacuum and freeze dried.

Analysis of Purified Fractions by HPLC/MS

To determine purity of the individual oligomeric fractions, an analysis was performed using a normal-phase high-performance chromatograph (HPLC) method interfaced with online mass spectrometry (MS) analysis using an atmospheric pressure ionization electrospray (API-ES) chamber as described by Lazarus et al. (1999), supra. Chromatographic analyses were performed on an HP 1100 series (Hewlett-Packard, Palo Alto, Calif.) equipped with an auto-injector, quaternary HPLC pump, column heater, diode array detector, and HP ChemStation for data collection and manipulation. Normal-phase separations of the procyanidin oligomers were performed on a Phenomenex (Torrance, Calif.) Luna silica column (25×4.6 mm) at 37° C. UV detection was recorded at a wavelength of 280 nm. The ternary mobile phase consisted of (A) dichloromethane, (B) methanol, and (C) acetic acid and water (1:1 v/v). Separations were effected by a series of linear gradients of B into A with a constant 4% of (C) at a flow rate of 1 mL/min as follows: elution starting with 14% of (B) into (A); 14–28.4% of (B) into (A), 0–30 min; 28.4–50% of (B) into (A), 30–60 min; 50–86% of (B) into (A), 60–65 min; and 65–70 min isocratic.

HPLC/MS analyses of purified fractions were performed using an HP 1100 series HPLC, as described above, and interfaced to an HP series 1100 mass selective detector (model G1946A) equipped with an API-ES ionization chamber. The buffering reagent was added via a tee in the eluant stream of the HPLC just prior to the mass spectrometer and delivered with an HP 1100 series HPLC pump, bypassing the degasser. Conditions for analysis in the negative ion mode included 0.75 M ammonium hydroxide as a buffering reagent at a flow rate of 0.04 mL/min, a capillary voltage of 3 kV, a fragmentor at 75 V, a nebulizing pressure of 25 psig, and a drying gas temperature at 350° C. Data were collected on an HP ChemStation using both scan mode and selected ion monitoring (SIM). Spectra were scanned over a mass range of m/z 100–3000 at 1.96 seconds per cycle. The ammonium hydroxide was used to adjust the eluant pH to near neutrality via an additional auxiliary pump just prior to entering the MS. This treatment counteracted the suppression of negative ionization of the (−)-epicatechin standard due to the elevated concentration of acid in the mobile phase. The purity for each fraction was determined by peak area, using UV detection at a wavelength of 280 nm in combination with a comparison of the ion abundance ratio between each oligomeric class.

Quantification of Procyanidins in Cocoa and Chocolate

A composite standard was made using commercially available (−)-epicatechin for the monomer. Dimers through decamers were obtained in a purified state by the methods described above. Standard stock solutions using these compounds were analyzed using the normal-phase HPLC method described above with fluorescence detection at excitation and emission wavelengths of 276 nm and 316 nm, respectively. Peaks were grouped and their areas summed to include contributions from all isomers within any one class of oligomers and calibration curves generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was de-fatted using three hexane extractions (45 mL each). Next, one gram of de-fatted material was extracted with 5 mL of the acetone/ water/acetic acid mixture (70:29.5:0.5 v/v). The quantity of procyanidins in the de-fatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

EXAMPLE

Human volunteers were instructed to fast overnight and to maintain low phytochemical intake the evening before the study. Phytochemicals are components in plants and foods derived from plants including many fruits, coffee, some teas, green peppers, garlic, onions, yogurt, bran, and cruciferous vegetables such as broccoli, cabbage, and cauliflower, etc.

Blood was drawn from the subjects prior to consumption of any food. The subjects ingested either semisweet or dark chocolate. The two different chocolates were used to demonstrate that the cocoa polyphenols could be delivered in different forms and still exhibit the same effects. The chocolates had different levels of chocolate liquor and sugars as defined by the Standard of Identity rules for semisweet chocolate and dark chocolate. The chocolate liquor used to make these products was prepared from a blend of beans, some of which were underfermented. After the initial blood was drawn, the subjects were divided into two groups. One group was tested with the semisweet chocolate and the other group was tested with the dark chocolate. Both chocolates had enhanced levels of cocoa procyanidins. The conserved levels were obtained by the process described herein.

For the dark chocolate experiment, the control subjects consumed a control bar which contained a low level of cocoa procyanidins, i.e., only 3.3 mg cocoa procyanidins (1.8 mg monomer) per 36.9 gram control product. The dark chocolate test product contained 147 mg total cocoa procyanidins (40.6 mg monomer) per 36.9 gram test product. Blood samples were drawn at 2 hours, after which another bagel was consumed. At 6 hours, another blood sample was drawn. FIG. 1 shows the nanomoles (nmol) of malondialdehyde (MDA) in plasma at 2 and at 6 hours following ingestion of ½ bagel with the dark chocolate test product or ½ bagel with the control chocolate product having the low cocoa procyanidins. As demonstrated by the data in FIG. 1, the higher the level of cocoa procyanidins ingested, the lower the levels of MDA in the plasma.

The control chocolate product which some of the subjects ingested was prepared from jet black cocoa powder that was approximately ten to twelve percent fat that was completely alkalized. The powder was reconstituted in cocoa butter to give the proper percentage fat in the dark chocolate test bar (taking into account the 9.87% fat in the powder itself). The control bar was formulated with 49.335% sugar, 19.75% jet black cocoa powder, 27.344% cocoa butter, 2.61% anhydrous milk fat, 0.06% vanillin, 0.75% lecithin, 0.15% prova vanilla, and 0.001% orange oil. The level of monomer was calculated to be 1.8 mg per bar based upon the 3.3 mg per bar level of cocoa procyanidins and the known levels of fat.

Figure 2:
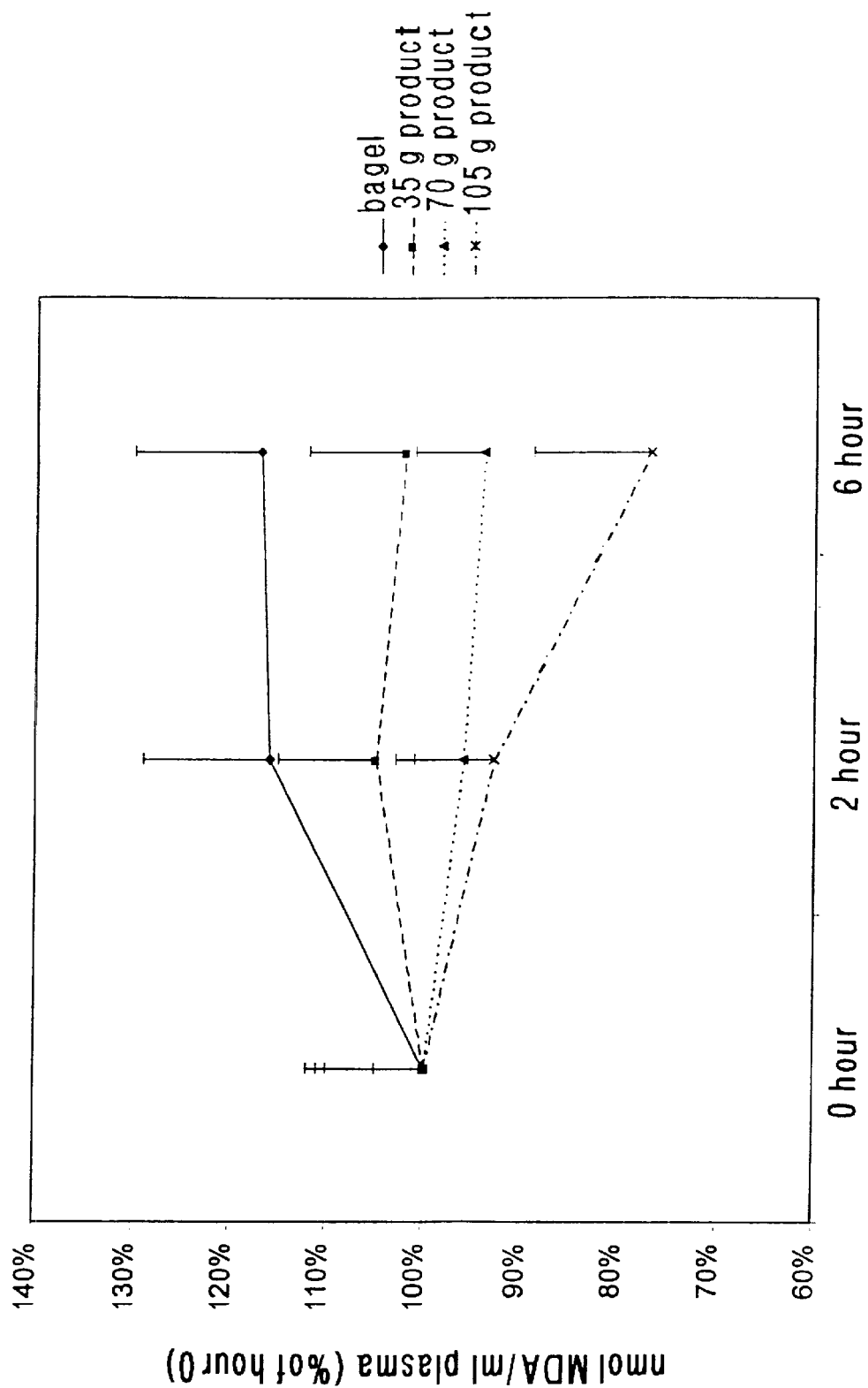
FIG. 2 shows the nanomoles (nmol) of malondialdehyde (MDA) in plasma at 2 and at 6 hours following ingestion of ½ bagel alone and following ingestion of ½ bagel with increasing quantities of semisweet chocolate which is typically high in cocoa polyphenols, including cocoa procyanidins (CPs).

For the semisweet experiment, the control subjects consumed ½ bagel alone and no chocolate. The test group consumed ½ bagel with one of three different chocolates, each with a different level of cocoa procyanidins per bag. The first chocolate test product was a 35 gram semisweet chocolate product containing 185 mg total cocoa procyanidins (45.3 mg monomer) per 35 grams. The second chocolate test product was a 70 gram semisweet chocolate product containing 370 mg total cocoa procyanidins. The third chocolate test product was a 105 gram semisweet chocolate product containing 555 mg total cocoa procyanidins. Blood samples were drawn at 2 hours, after which another bagel was consumed. After 6 hours, another blood sample was drawn. FIG. 2 shows the nanomoles (nmol) of malondialdehyde (MDA) in plasma at 2 and at 6 hours following ingestion of ½ bagel alone and following ingestion of ½ bagel with increasing quantities of semisweet chocolate product, i.e., 35, 70 and 105 grams, containing increasing quantities of total cocoa procyanidins, i.e., 185, 370 and 555 mg. As demonstrated by the data in FIG. 2, the higher the level of cocoa procyanidins ingested, the lower the levels of MDA in the plasma.

For the analysis of the thiobarbituric reactive substances (TBARS), a plasma sample (100 L) was mixed with 4% butylated hydroxytoluene (BHT) and then frozen overnight. The sample was then thawed at room temperature and a 100 L sample was mixed with 200 L sodium dodecyl sulfate (SDS). The following reagents were then added in sequence: 800 L 0.1 N hydrochloric acid (HCl), 100 L 10% 1,4-benzenedicarboxylic acid (PTA), and 400 L 0.7% thiobarbituric acid (TBA). The sample mixture was incubated in 95° C. water bath for 30 minutes. After cooling on ice, 1 ml of 1-butanol was added. The sample was then centrifuged for 10 minutes at 1800 g (3000 rpm) at 4 C. A 200 L aliquot of the butanol phase was assayed for extracted MDA by fluorometry. This quantity was used for each of the 96 wells of the plate which was read with excitation at 515 nm, slit 5 nm and emission at 555 nm, slit 5 nm.

The effect of the cocoa procyanidin levels on the oxidative stress, as measured by the TBARS assay, was apparent at 2 hours and at 6 hours as shown by the change in total nanomoles of MDA per milliliters of plasma. Whether the cocoa procyanidins were present in the dark chocolate test product or in the semisweet chocolate test products made no difference. In addition, the effect was more pronounced as the amounts of total cocoa procyanidins consumed increased.

What is claimed is:

1. A method for treating a mammal suffering from or at risk to suffer from atherosclerosis, by reducing postprandial oxidative stress in the mammal, which method comprises having the mammal consume an effective amount of a cocoa polyphenol.

2. The method of claim 1, wherein the cocoa polyphenol is cocoa procyanidins.

3. The method of claim 2, wherein the cocoa procyanidins are monomers and/or oligomers of catechin and epicatechin.

4. The method of claim 3, wherein the oligomers are dimers through octadecamers.

5. The method of claim 1, wherein the cocoa polyphenols are present in a food, a dietary supplement, or a pharmaceutical.

6. The method of claim 5, wherein the food is a beverage.

7. The method of claim 5, wherein the food is a confectionery.

8. The method of claim 5, wherein the dietary supplement further comprises a nutrient or a carrier.

9. The method of claim 5, wherein the pharmaceutical further comprises a carrier, a diluent, or an excipient.

10. The method of claim 7, wherein the confectionery is a chocolate.

11. The method of claim 5, wherein the food is a chocolate prepared using cocoa ingredients which are prepared from cocoa beans or blends thereof having a fermentation factor of 275 or less.

12. The method of claim 11, wherein the cocoa ingredients are selected from the group consisting of chocolate liquor, cocoa solids, roasted cocoa nibs or nib fractions, or a solvent-derived cocoa extract.

13. The method of claim 10, wherein the chocolate is a dark chocolate.

14. The method of claim 13, wherein the dark chocolate is a bittersweet, semisweet, or sweet dark chocolate.

15. The method of claim 14, wherein the chocolate is a Standard of Identity chocolate.

16. The method of claim 14, wherein the chocolate is a non-Standard of Identity chocolate.

17. The method of claim 10, wherein the chocolate is a milk chocolate, buttermilk chocolate, skim milk chocolate or mixed dairy milk chocolate.

18. The method of claim 10, wherein the chocolate is a reduced-fat chocolate.

19. The method of claim 17, wherein the chocolate is a Standard of Identity chocolate.

20. The method of claim 17, wherein the chocolate is a non-Standard of Identity chocolate.

21. The method of claim 10, wherein the chocolate is a white chocolate or a white chocolate coating.

22. The method of claim 11, wherein the cocoa ingredients are prepared from underfermented beans or mixtures of fermented beans and underfermented and/or unfermented beans.

23. A method of reducing the risk of pathologies associated with oxidative stress in a mammal suffering from atherosclerosis, which method comprises having the mammal consume an amount of a cocoa polyphenol effective to reduce oxidative stress.

24. The method of claim 23, wherein the associated pathologies are selected from the group consisting of coronary heart diseases, neurodegenerative disorders, and cancer.

25. The method of claim 2, wherein the cocoa procyanidins comprise monomeric and/or oligomeric fractions.

26. The method of claim 25, wherein the cocoa procyanidins are pooled fractions.

27. The method of claim 5, wherein the food, the dietary supplement, or the pharmaceutical is prepared using cocoa ingredients prepared from slaty cocoa beans, purple cocoa beans, mixtures of slaty and purple cocoa beans, mixtures of purple and brown cocoa beans, or mixtures of slaty, purple, and brown cocoa beans.

28. The method of claim 5, wherein during the preparation of the food, milk and/or sweetener is protected by pretreatment with an antioxidant, an emulsifier, a fat, a flavorant, or mixtures thereof.

29. The method of claim 28, wherein the pretreated ingredients comprise a mixture of cocoa butter and lecithin.

30. The method of claim 29, wherein the food is a pet food, a dry cocoa mix, a pudding, a syrup, a cookie, a savory sauce, a rice mix, a rice cake, a cocoa beverage, a carbonated beverage, a chocolate confectionery, a cocoa and a nut based product, a nut-based product, or a low-fat food.

31. The method of claim 30, wherein the chocolate confectionery is a reduced fact chocolate, a dark chocolate, a milk chocolate, or a white chocolate.

32. A method of treating a mammal suffering from or at risk of suffering from post-prandial oxidative stress by administering to the mammal an amount of at least one cocoa polyphenol effective to reduce post-prandial oxidative stress.

* * * * *